US008911344B2

(12) United States Patent
Altan et al.

(10) Patent No.: US 8,911,344 B2
(45) Date of Patent: Dec. 16, 2014

(54) VAGINAL INSERT DEVICE HAVING PERPENDICULAR SEGMENTS

(75) Inventors: Amanda Rae Altan, Kaukauna, WI (US); MaryAnn Zunker, Oshkosh, WI (US); Sarah Anne Olson, Appleton, WI (US); Christine Marie Cowell, Neenah, WI (US); Jennifer Leigh Skabroud Misek, Neenah, WI (US); Chadwick Irvin Romzek, Neenah, WI (US); Matthew Edward Gerstle, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 446 days.

(21) Appl. No.: 13/331,107

(22) Filed: Dec. 20, 2011

(65) Prior Publication Data

US 2013/0158340 A1 Jun. 20, 2013

(51) Int. Cl.
*A61F 2/82* (2013.01)
*A61F 2/00* (2006.01)

(52) U.S. Cl.
USPC .......... 600/30

(58) Field of Classification Search
CPC .......... A62F 2/0004–2/0054; A62F 6/08; A62F 6/12
USPC .......... 600/29–31; 128/834–841
See application file for complete search history.

(56) References Cited

U.S. PATENT DOCUMENTS 3,780,730 A * 12/1973 Weisman .......... 128/832
4,031,886 A * 6/1977 Morhenn .......... 128/837
6,013,023 A * 1/2000 Klingenstein .......... 600/29
6,090,038 A 7/2000 Zunker et al.
6,460,542 B1 10/2002 James
6,676,594 B1 1/2004 Zunker et al.
2002/0083949 A1* 7/2002 James .......... 128/830
2008/0033230 A1* 2/2008 Bartning et al. .......... 600/29
2008/0149109 A1* 6/2008 Ziv .......... 128/834

FOREIGN PATENT DOCUMENTS

WO WO 97/43982 A1 11/1997
WO WO 2011/079124 A1 6/2011

* cited by examiner

*Primary Examiner* — Charles A Marmor, II
*Assistant Examiner* — Catherine B Kuhlman
(74) *Attorney, Agent, or Firm* — Kimberly-Clark Worldwide, Inc.

(57) ABSTRACT

A vaginal insert device includes a support segment having a distal end and a proximal end, the support segment defining a support segment plane; and a stabilizing segment extending from the distal end of the support segment, the stabilizing segment defining a stabilizing segment plane, wherein the stabilizing segment plane is generally perpendicular to the support segment plane when the vaginal insert device is in an in-use configuration. A vaginal insert device system including the vaginal insert device can also include an applicator coupled to the vaginal insert device when the vaginal insert device is in an insertion configuration.

16 Claims, 6 Drawing Sheets

110 104 L2 108 140 L1 102 112 100 106 D2 160

100
202
110
104
150
108
112
102
160

202
100
150
110
104
108
112
102
D1
160

VAGINAL INSERT DEVICE HAVING PERPENDICULAR SEGMENTS

BACKGROUND

Female stress urinary incontinence (SUI), the involuntary loss of urine, can occur during normal movements and everyday activities including laughing, coughing, sneezing, exercise and any physical activity that causes an increase in intra-abdominal pressure resulting in urine to flow from the bladder through the urethral tube to the outside of the body. The primary causative factor resulting in genuine stress incontinence is the incomplete transmission of abdominal pressure to the proximal urethra due to the displacement of the urethra from its intra-abdominal position. Stress incontinence is related to weakened pelvic floor muscles tissue and ligaments that are no longer able to adequately support the proximal urethra and elevate it above the pelvic floor thereby subjecting it to increases in intra-abdominal pressure, thus allowing compression and maintenance of continence [Urogynecology and Urodynamics—Theory and Practice, chapter 36, page 494]. Stress incontinence can result from repetitive straining of the pelvic muscles, pregnancy, obesity etc. that lead to a loss of pelvic muscle tone and other medical causes that can also occur naturally with the aging process. Some women, especially women who have given birth to one or more children, and older women, can experience incidences of involuntary urine loss due to stress urinary incontinence or combined stress and urge incontinence.

As the world's female population ages, there is an ever-increasing need for a consumer friendly, method or measure to reduce the involuntary urine loss commonly associated with stress urinary incontinence. Although there are specialized products available for this purpose, many can only be purchased with a prescription and they need to be properly sized, physically inserted and/or adjusted by a medical practitioner for them to perform correctly. Over the counter solutions like feminine pads and incontinence pads being bulky and exterior to the body are not discreet and do not mitigate the problem before absorbent protection is required.

In view of the lack of commercially-available devices that are easy to use, there is a need for a urinary incontinence device that can be purchased by the consumer and that is uncomplicated and user friendly. Furthermore, there is a need for a urinary incontinence device that is easy for a woman to insert into and remove from her body that is comfortable to wear and provides both physical and psychological assurance that it is capable of properly performing over an extended period of time.

SUMMARY

Generally, a vaginal insert device used to treat urinary incontinence is disclosed. The vaginal insert device includes a support segment, a stabilizing segment, and a removal device. The vaginal insert device expands in the vagina to deliver an outward compression force against the bladder neck via the anterior vaginal wall to assist in the prevention of stress urinary incontinence.

In an exemplary aspect, the stabilizing segment is attached to the distal end of the support segment. The stabilizing segment provides a means to prevent the vaginal insert device from unintentionally moving, thereby stabilizing the vaginal insert device within the vaginal cavity.

In another aspect, a removal member can be attached to the vaginal insert device. The removal member can be anything known by one skilled in the art to allow a user to remove the vaginal insert device.

The vaginal insert device has three separate configurations depending on whether the device is being inserted, is in-use, or is being removed. Accordingly, the vaginal insert device has an insertion configuration, an in-use configuration, and a removal configuration. The insertion configuration can include the vaginal insert device being compressed and folded inward so that the largest outer dimension of the vaginal insert device has an insertion diameter.

After insertion of the vaginal insert device into the vaginal cavity, the vaginal insert device expands to a maximum shape to transition between the insertion configuration and the in-use configuration wherein the largest outer dimension of the vaginal insert device has an in-use diameter larger than the insertion diameter.

Desirably, the vaginal insert device can be stored in the insertion configuration within an applicator. The applicator maintains the vaginal insert device in the insertion configuration, and removal of the vaginal insert device from the applicator transitions the vaginal insert device from the insertion configuration to the in-use configuration.

In exemplary aspects, when the vaginal insert device is in the removal configuration, the largest outer dimension of the vaginal insert device has a removal diameter that is the same size as the in-use diameter. In other aspects, the vaginal insert device becomes elongated when the removal member is activated so that the largest outer dimension of the vaginal insert device has a removal diameter smaller than the in-use diameter. Desirably, the removal member comprises a string, and tension on the string compels the vaginal insert device to an elongated position in transition between the in-use configuration and the removal configuration.

Desirably, the vaginal insert device is constructed of a compliable resilient material.

In one aspect, the vaginal insert device includes a support segment having a distal end and a proximal end, the support segment defining a support segment plane; and a stabilizing segment extending from the distal end of the support segment, the stabilizing segment defining a stabilizing segment plane, wherein the stabilizing segment plane is generally perpendicular to the support segment plane when the vaginal insert device is in an in-use configuration.

In another aspect, a vaginal insert device system includes a vaginal insert device including a support segment having a distal end and a proximal end, the support segment defining a support segment plane, and a stabilizing segment extending from the distal end of the support segment, the stabilizing segment defining a stabilizing segment plane, wherein the stabilizing segment plane is generally perpendicular to the support segment plane when the vaginal insert device is in an in-use configuration. The system also includes an applicator coupled to the vaginal insert device when the vaginal insert device is in an insertion configuration.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
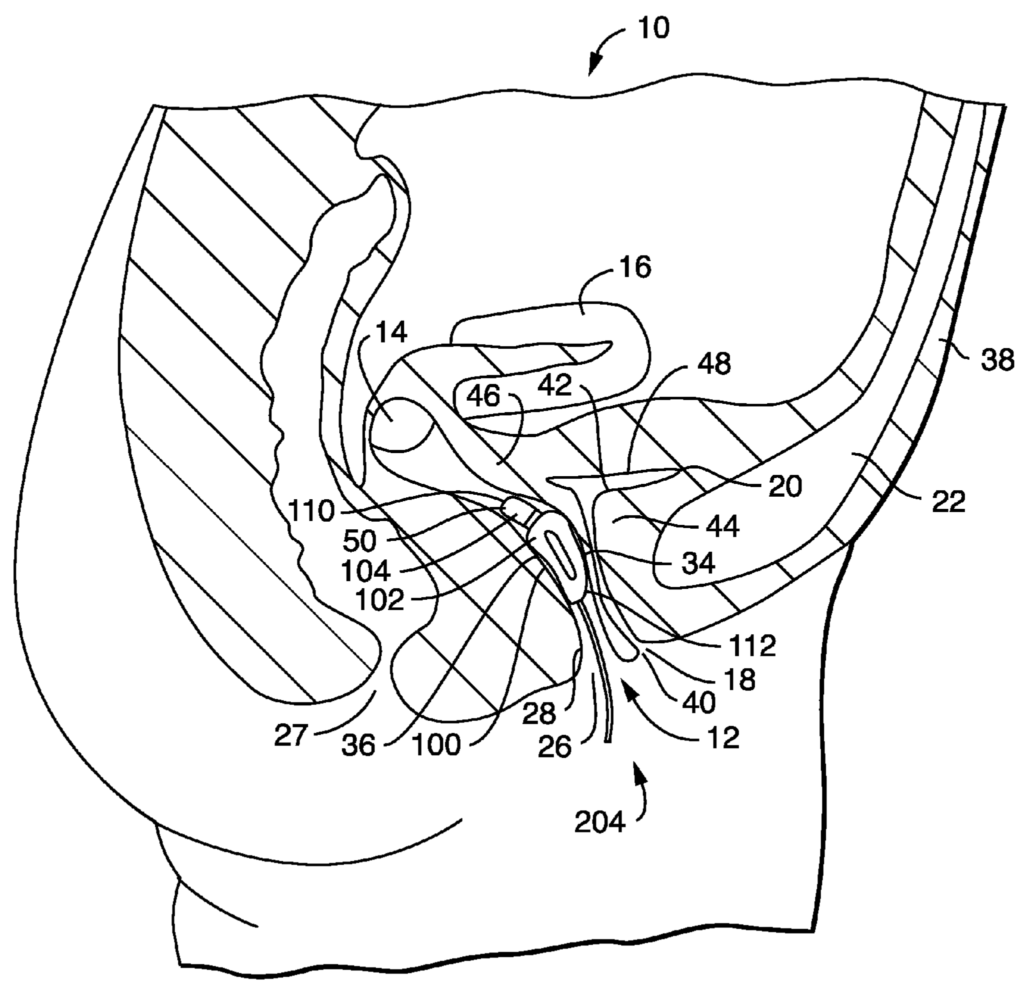
FIG. 1 is a mid-sagittal section of a human torso showing one aspect of a vaginal insert device positioned in the vaginal canal showing the support segment of the vaginal insert device aligned with the bladder neck region to cooperate with the symphysis pubis to allow the urethral tube to be compressed upon itself and alleviate urinary incontinence during episodes of increased intra-abdominal pressure.
Figure 2A:
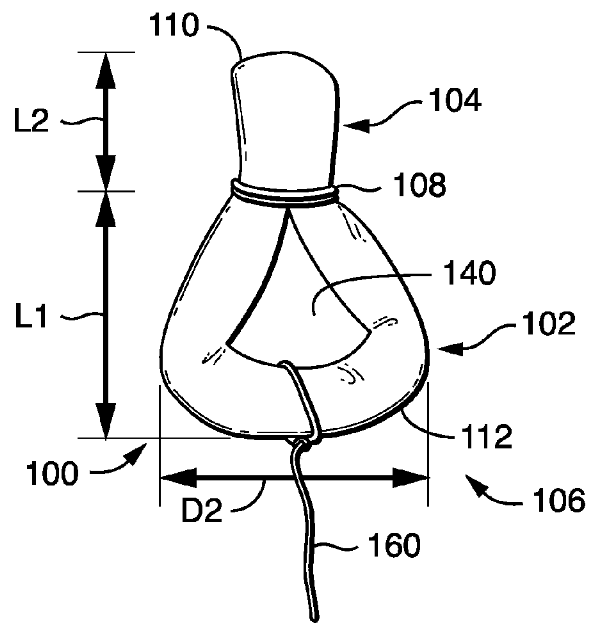
FIG. 2A is a perspective view of one aspect of the vaginal insert device of FIG. 1 in an as-manufactured or relaxed configuration.
Figure 2B:
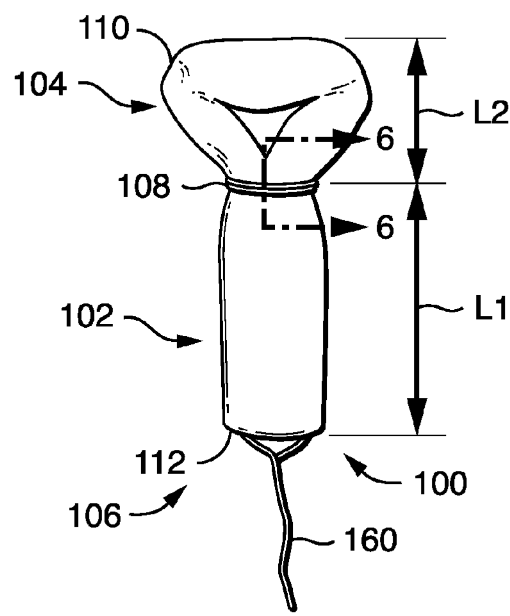
FIG. 2B is a perspective view of the aspect of the vaginal insert device of FIG. 2A, rotated 90 degrees from FIG. 2A to show additional features.
Figure 2C:
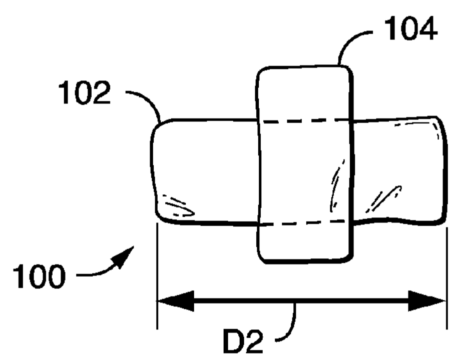
FIG. 2C is a perspective top view of the aspect of the vaginal insert device of FIG. 2A.
Figure 2D:
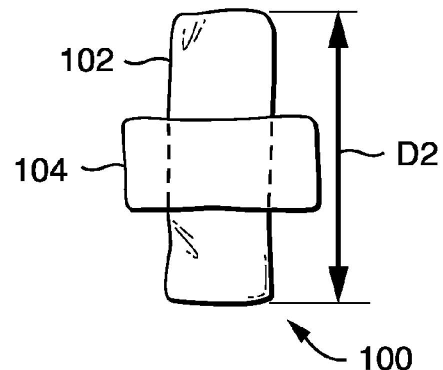
FIG. 2D is a perspective top view of the aspect of the vaginal insert device of FIG. 2B.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

Many women do not seek treatment for SUI because of the social stigma associated with incontinence and because most women do not feel that their urine leakage is bad enough to be called incontinence. The management of SUI is largely determined by the severity of her SUI and by how much the disorder interferes with her everyday life. Treatments for SUI can the divided into several categories: behavioral changes, medication, pelvic floor muscle training, vaginal pessaries, and surgical procedures.

An alternative approach to alleviate incontinence uses vaginal insert devices that are designed to support the area of the urethra and bladder neck to manage SUI. To provide proper support, the device needs to be properly placed and then maintained in its position during use. Proper placement is achieved using an applicator. Proper functionality can be achieved through several mechanisms of action: 1) deliver support to the bladder neck region so that the urethra remains closed during laughs, coughs, sneezes, or physical exertion; 2) allowing transmission of sufficient pressure across the interior wall of the vagina causing the opposing walls of the urethra to come into intimate contact with each other, thereby preventing or diminishing the escape of urine from the body; 3) creating a pivot point to intentionally cause the urethra to form a kink just below the bladder neck (when abdominal pressure increases, thrusting the bladder forward and downward where the transitory kinking prevents the escape of urine until the abdominal pressure subsides); 4) a combination of any two or more of these mechanisms.

The present disclosure provides this proper support through the use of a device that is designed to have no radial directionality in use, thereby ensuring proper positioning through a unique, packaged configuration (vaginal insert device inside the applicator) and is therefore able to be positioned inside the vagina while allowing for deployment of a unique stabilization feature.

Generally, a vaginal insert device used to treat urinary incontinence is disclosed. The vaginal insert device includes a support segment, a stabilizing segment, and a removal device.

Turning now to FIG. 1, a human torso 10 of a female is shown with a vagina 12, a cervix 14, a uterus 16, a urethra 18, a bladder 20 and a symphysis pubis 22. The vagina 12 has an introital opening 24 that exits the human body 10 and contains a vaginal canal 26 that extends from the introital opening 24 to the cervix 14. The vaginal canal 26 has a length that ranges from between about 4 inches to about 6 inches (about 102 to about 153 mm) in most women. The cervix 14 is the entrance to the uterus 16 and is located between the upper aspect of the vaginal canal 26 and the uterus 16. The rectum 27 is located posterior to the vagina 12. The vaginal canal 26 has an inner periphery 28.

Figure 4:
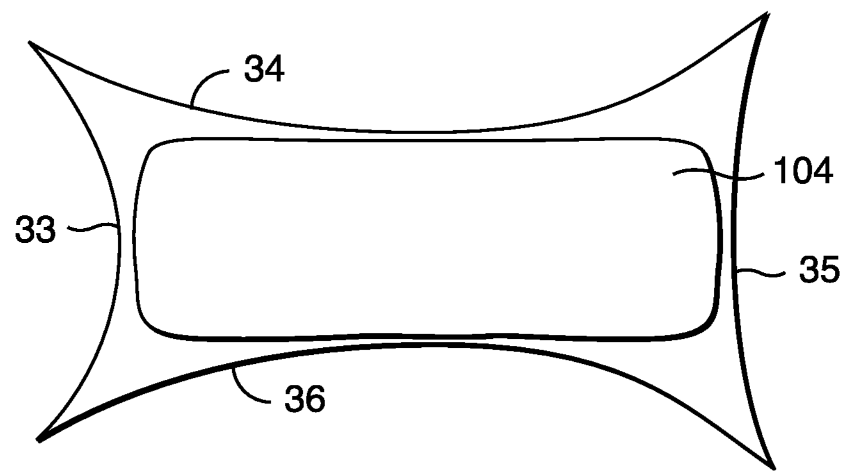
FIG. 4 is a partial cross section view showing the aspect of the vaginal insert device of FIG. 1 in an in-use configuration.
Figure 5A:
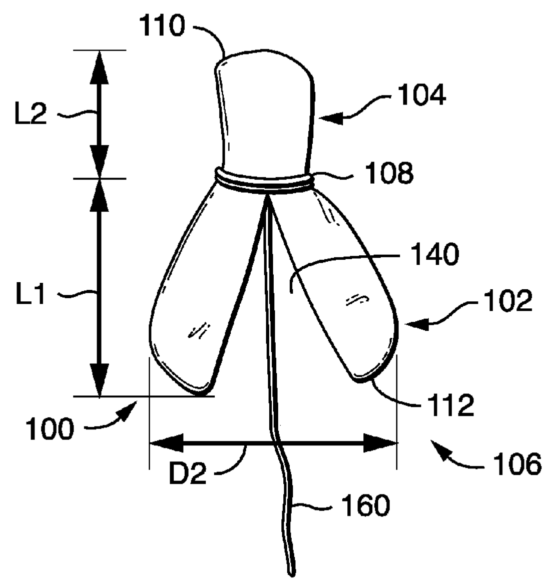
FIG. 5A is a perspective view of one aspect of the vaginal insert device of FIG. 1 in an as-manufactured or relaxed configuration.
Figure 5B:
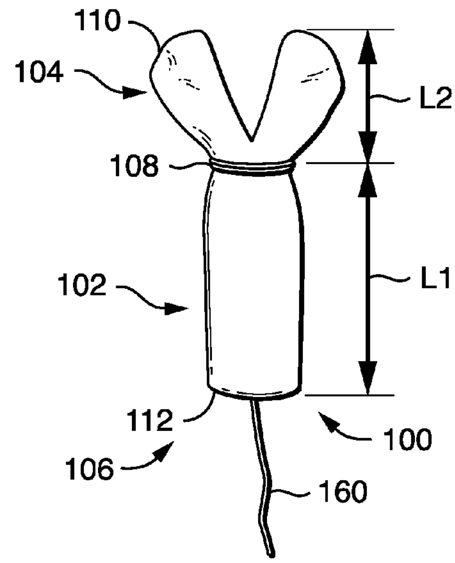
FIG. 5B is a perspective view of the aspect of the vaginal insert device of FIG. 5A, rotated 90 degrees from FIG. 5A to show additional features.
Figure 5C:
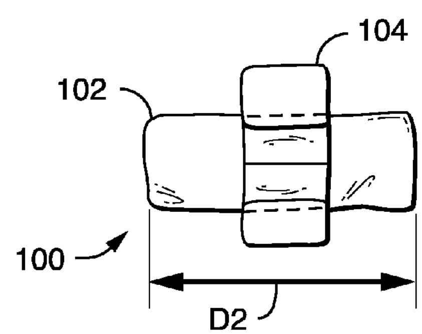
FIG. 5C is a perspective top view of the aspect of the vaginal insert device of FIG. 5A.
Figure 5D:
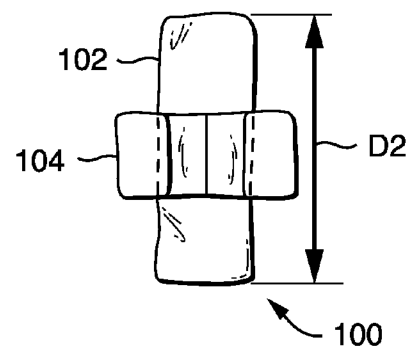
FIG. 5D is a perspective top view of the aspect of the vaginal insert device of FIG. 5B.

The inner periphery 28 is made up of a right lateral wall 33 (see FIG. 4), a left lateral wall 35 (see FIG. 4), an anterior wall 34, and a posterior wall 36. The four walls encompass the entire 360 degrees of the inner periphery 28. The anterior wall 34 is located closest to the urethra 18 and the urethra 18 is located between the symphysis pubis 22 and the vagina 12.

The vaginal canal 26 can be divided into three approximately equal sections, each representing about one-third of the overall length. Each section is approximately 2 inches (approximately 51 mm) in length. The middle third of the vaginal canal 26 is the most important section for alleviating female urinary incontinence because of its proximity to the urethra 18 and is the location where a vaginal insert device should be positioned. The middle third of the vaginal canal 26 is also horizontally offset from the symphysis pubis 22, which is a bony prominence situated adjacent to a front portion 38 of the human torso 10 and can be referred to as the bladder neck region 50. Cooperation between a vaginal insert device positioned in the vagina 12 and the symphysis pubis 22 allows the urethra 18 to be compressed upon itself thereby providing a means to alleviate involuntary urine flow from the bladder.

The urethra 18, also referred to as a urethral tube, is a hollow tubular structure that extends from a first opening 40 that exits the human body 10 to a second opening 42 situated at the lower surface of the bladder 20. The urethra 18 has a length of about 1.5 inches (about 38 mm) in most women. The urethra 18 functions to discharge urine, which is temporarily stored in the bladder 20, from the human body. The urethra 18 has a plurality of urethral sphincter muscles 44 located along the length of its inner periphery 28. The urethral sphincter muscles 44 are situated below the second opening 42 and are ring like muscles that normally maintain constriction of the urethra 18 to prevent the passage of urine. The relaxation of the urethral sphincter muscles 44 by normal physiological functioning will permit urine to be voluntarily expelled from the body.

Again, referring to FIG. 1, the human torso 10 further includes musculature and body tissue located in the urethrovaginal myofascial area 46 that is situated between the vagina 12 and the symphysis pubis 22. The bladder 20 lies posterior to the symphysis pubis 22 and is separated from the rectum 27 by the vagina 12 and the uterus 16. The ureters (not shown) that transport urine from the kidneys to the bladder 20, pass from the pelvis to the posterior aspect of the urinary bladder 20. The fundus vesicae 48, into which both of the ureters terminate, is located adjacent to the anterior wall 34 of the vagina 12.

A vaginal insert device 100 is shown positioned in the vaginal canal 26 and, in particular, in the bladder neck region 50. The vaginal insert device 100 is designed to bridge across the vagina to support the musculature and body tissue located in the urethra-vaginal myofascial area 46. In other words, the vaginal insert device 100 and, in particular, the support segment 102 supports the bladder neck 50 to a more normal retropubic position thereby restoring continence.

The vaginal insert device 100 is shown in use. A portion of the vaginal insert device 100 and, in particular, the support segment 102 of the vaginal insert device 100 is directly touching the anterior and posterior walls 34 and 36. Alternatively, the vaginal insert device 100 can be selectively positioned such that a portion of the vaginal insert device 100 can be touching both the right and left lateral walls 33, 35 and the anterior and posterior walls 34, 36 (see FIG. 4) to provide a supportive backdrop for the urethral tube 18 and to support the bladder neck region 50, thereby restoring continence. The urethral tube 18 will now be sufficiently compressed to intercept the flow of urine and to provide support to the urethral sphincter muscle 44 so that it can function properly. By permitting the urethral tube 18 to be compressed upon itself between the vaginal insert device 100 and the symphysis pubis 22, the involuntary flow of urine from the bladder is limited.

Figures 3A, 3B:
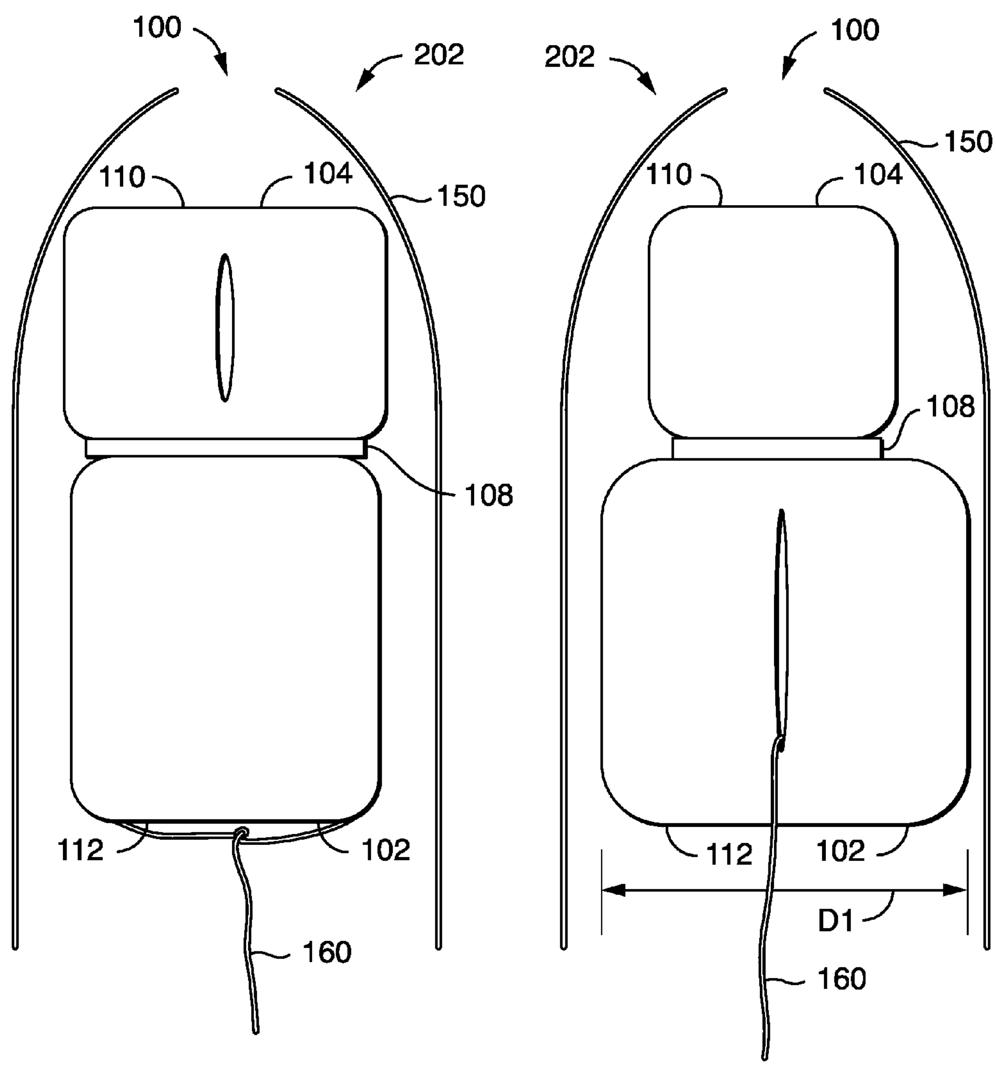
FIG. 3A is a partially cutaway schematic view of the aspect of the vaginal insert device of FIG. 1 in an insertion configuration.
FIG. 3B is a partially cutaway schematic view of the aspect of the vaginal insert device of FIG. 3 in an insertion configuration, rotated 90 degrees from FIG. 3A to show additional features.

Referring now to FIGS. 2 and 3, the vaginal insert device 100 includes a support segment 102, a stabilizing segment 104, and a removal member 160. Each of the support and stabilizing segments 102, 104 is a torus. It should be noted that torus in the present usage is not limited to a strict geometric definition including symmetry and consistent dimensions. "Torus" is used herein to refer to a portion of the vaginal insert device 100 that, in a relaxed state, is a generally doughnut-shaped polyhedron or closed loop having a torus inside diameter, a torus outside diameter, and a tube diameter, which is the diameter of one side of the torus in a cross-section view. The shape and dimensions can vary, particularly when the vaginal insert device 100 is compressed into an applicator, when the vaginal insert device 100 is conforming to a particular vaginal canal 26, and when the vaginal insert device 100 is being withdrawn from the vaginal canal 26. The torus shape can have a variety of cross-sectional shapes including any polygon such that a toroid is formed. If the support segment 102 has a non-round cross section, the outside diameter of the support segment 102 can be defined by connecting the outermost points of the cross-sectional area. Typically, the support segment 102 has a substantially round cross-section.

As shown in FIGS. 2A-D, the support segment 102 has a longitudinal length L1 and the stabilizing segment 104 has a longitudinal length L2. L1 can be equal to L2, or L1 can be less than L2. L1 is preferably larger than L2.

In an alternative aspect of the present disclosure shown in FIG. 5, a vaginal insert device 250 includes a support segment 252, a stabilizing segment 254, and a removal member 260. Each of the support and stabilizing segments 252, 254 is an open V shape of the same general construction and dimensions as the tori described herein. The shape and dimensions can vary, particularly when the vaginal insert device 250 is compressed into an applicator, when the vaginal insert device 250 is conforming to a particular vaginal canal 26, and when the vaginal insert device 250 is being withdrawn from the vaginal canal 26. The V-shaped support and stabilizing segments 252, 254 can have a variety of cross-sectional shapes including any polygon. If the support segment 252 has a non-round cross section, the outside diameter of the support segment 252 can be defined by connecting the outermost points of the cross-sectional area. Typically, the support segment 252 has a substantially round cross-section.

As shown in FIGS. 5A-D, the support segment 252 has a longitudinal length L1 and the stabilizing segment 254 has a longitudinal length L2. L1 can be equal to L2, or L1 can be less than L2. L1 is preferably larger than L2.

Although the description herein of the vaginal insert device 100, 250 will focus primarily on the aspect of the dual tori of FIGS. 2 and 3, the description herein is equally applicable to the V-shaped aspect of FIG. 5. The vaginal insert device 100 provides for generating urethral support and has a distal end 110 and a proximal end 112. As used in the specification and claims, the distal end 110 of the vaginal insert device 100 refers to the end in the direction of the cervix 14, or that portion that is first inserted into the vagina 12. As used in the specification and claims, the proximal end 112 of the vaginal insert device 100 itself refers to the end in the direction of the introital opening 24, or that portion that is last inserted into the vagina 12. The vaginal insert device 100 has three separate configurations depending on whether the device is being inserted, is in-use, or is being removed. Accordingly, the vaginal insert device 100 has an insertion configuration 202, an in-use configuration 204, and a removal configuration (not shown).

As a point of reference, the vaginal insert device 100 is illustrated in FIG. 2 in an as-manufactured or relaxed configuration. The support segment 102 and the stabilizing segment 104 can be manufactured as separate segments and coupled in any suitable manner, or can be manufactured as separate portions of the same tube of material. In one example, the support and stabilizing segments 102 and 104 can be portions of a single device torus 106, wherein one side of the device torus 106 is attached to an opposite side of the device torus 106 to form the support and stabilizing segments 102, 104. In one aspect, one side of the device torus 106 can be attached to the opposite side of the device torus 106 to form a central joint 108, such as by tying a string around the device torus 106 as shown in FIG. 2.

Figure 6:
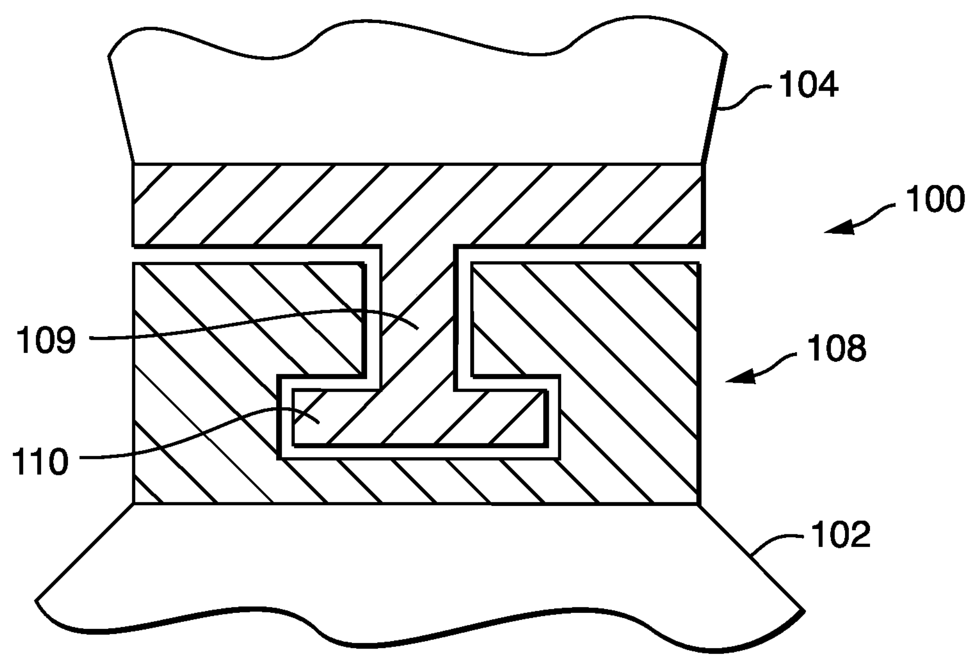
FIG. 6 is a partial cross section schematic view of a central joint of the vaginal insert device taken at the 6-6 line of FIG. 2B.

In another aspect of the present disclosure, the central joint 108 can be the juncture of separate support and stabilizing segments 102, 104. In one example illustrated in FIG. 6, the central joint 108 can include a key 109 and a keyway 110 to allow the stabilizing segment 104 to rotate with respect to the support segment 102. Any other suitable rotational mechanism can be employed at the central joint 108.

The vaginal insert device 100 is preferably manufactured such that the plane defined by the support segment 102 is generally perpendicular to the plane defined by the stabilizing segment 104 when the vaginal insert device 100 is in an as-manufactured or relaxed configuration, as is described in further detail below.

Accordingly, the vaginal insert device 100 has an insertion configuration 202, an in-use configuration 204, and a removal configuration.

In the insertion configuration 202 depicted in FIG. 3, vaginal insert device 100 is compressed to fit within an applicator 150, which is similar or identical to a standard tampon applicator known in the art. In the insertion configuration 202, the support segment 102 can be parallel with the stabilizing segment 104, coplanar with the stabilizing segment 104, perpendicular to the stabilizing segment 104, or in any other suitable geometry.

In the in-use configuration 204 depicted in FIG. 1, the vaginal insert device 100 with a distal end 110 and a proximal end 112 expands from the insertion configuration 202 to provide a dual segment shape as the vaginal insert device 100 is inserted into the vaginal canal 26. In the in-use configuration 204, the support segment 102 is preferably perpendicular to the stabilizing segment 104. In the aspects in which the support segment 102 is parallel to or coplanar with the stabilizing segment 104 while in the insertion configuration 202, the support segment 102 and the stabilizing segment 104 will transition from parallel or coplanar to being perpendicular as the vaginal insert device 100 transitions from the insertion configuration 202 to the in-use configuration 204.

As the vaginal insert device 100 transitions from the insertion configuration 202 to the in-use configuration 204, the individual elements of the support segment 102 and the stabilizing segment 104 expand relative to each other and individually. As the vaginal insert device 100 is expelled from the applicator 150, each of the support segment 102 and the stabilizing segment 104 expands in overall size from their compressed states. In addition, the tubes from which each of the support segment 102 and the stabilizing segment 104 are formed also expand in their diameters such that the tubes appear to be thicker or greater in cross-section dimension.

This dual expansion of both the support segment 102 and the stabilizing segment 104 increases the engagement area between the outer surface area of the vaginal insert device 100 and the mucosal lining of the vagina, allowing the support segment 102 and the stabilizing segment 104 to better engage such that the vaginal insert device 100 can maintain its optimal position through repeated exposure to exertions of varying (intra-abdominal) forces over prolonged periods of wear time.

Compression of the vaginal insert device 100 into an applicator 150 and its subsequent expulsion and expansion can be facilitated by the creation of pleats or indentations within and along the tubes of the support segment 102 and the stabilizing segment 104 to allow for collapsing the structure upon itself while in the applicator 150. The expanding stabilizing segment 104 maximizes contact with convex shape of vaginal walls without distorting them, while the support segment 102 is configured to apply pressure against urethra 18.

The support segment 102 and the stabilizing segment 104 each has a longitudinal length and a lateral outside dimension. In one aspect of the present disclosure, the longitudinal length of the stabilizing segment 104 is the same as the longitudinal length of the support segment 102. In another aspect of the present disclosure, the longitudinal length of the stabilizing segment 104 is less than the longitudinal length of the support segment 102. In still another aspect of the present disclosure, the longitudinal length of the stabilizing segment 104 is greater than the longitudinal length of the support segment 102.

In addition, it is preferred that the shape of the vaginal insert device 100 does not present any sharp corners or surfaces but instead is shaped to present rounded or curved surfaces to minimize any discomfort during insertion, use, and removal of the vaginal insert device 100. Accordingly, the edges of both the distal end 110 and the proximal end 112 of the vaginal insert device 100 are rounded. The rounded edge of the proximal end 112 of the vaginal insert device 100 allows for easier removal.

While the vaginal insert device 100 is in the in-use configuration 204, the device not including the removal member can have a longitudinal length of from about 10 to about 120 mm, desirably from about 30 to about 90 mm, and most desirably from about 50 to about 70 mm. The largest outer dimension of the device can also have a cross-sectional area from about 10 to about 70 mm, preferably from about 30 to about 60 mm.

FIG. 3 illustrates the vaginal insert device 100 with the support segment 102 and the stabilizing segment 104 in the insertion configuration 202. When the support segment 102 is in the insertion configuration 202, the support and stabilizing segments 102, 104 are compressed or folded inward. When the support and stabilizing segments 102, 104 are compressed and/or folded inward, the largest outer dimension of the support segment 102 can have an insertion diameter, D1, that allows for easier insertion into the vagina 12. Typically, the distal end 110 of the vaginal insert device 100 will compress to provide a substantially cylindrical shape with a uniform diameter throughout the vaginal insert device 100.

Typically, to allow for easy insertion into the vagina 12, the insertion diameter, D1, is smaller than the in-use diameter, D2. Desirably, the vaginal insert device 100 has an insertion diameter, D1, ranging from 10 to about 25 mm, preferably about 10 to about 20 mm, or more preferably about 15 to about 20 mm. The smaller insertion diameter, D1, of the vaginal insert device 100 provides an easier way to insert the vaginal insert device 100.

The support segment 102 also includes a fluid passageway 140. The fluid passageway 140 serves two important functions. First, the fluid passageway 140 provides the space necessary in the vaginal insert device 100 to allow the vaginal insert device 100 to compress inward to provide a smaller diameter when in the insertion configuration 202.

Secondly, the fluid passageway 140 is provided to facilitate the natural movement of vaginal fluids entering the vaginal insert device 100. More preferably, the fluid passageway 140 is defined by the space 140 extending through the vaginal insert device 100 from the distal end 110 and terminating at the proximal end 112.

As discussed above, there is a stabilizing segment 104 attached to the distal end 110 of the support segment 102. The stabilizing segment 104 provides a means to prevent the vaginal insert device 100 from unintentionally moving, thereby stabilizing the vaginal insert device 100 within the vaginal cavity. In an exemplary aspect of the present disclosure, the stabilizing segment 104 does not apply significant pressure to the wearer's vagina and/or urethra, thereby enhancing comfort.

Other structures known in the art can be provided as a stabilizing segment 104 to help stabilize the vaginal insert device 100 in the vagina and prevent the vaginal insert device 100 from unintentionally moving. Typically, the stabilizing segment 104 can have an outside diameter ranging from 10 to about 25 mm, preferably about 10 to about 20 mm, or more preferably about 15 to about 20 mm.

In addition, the vaginal insert device 100 also includes a removal member 160 attached to the vaginal insert device 100. The removal member 160 can be anything known in the art to allow a user to remove the vaginal insert device 100 from the vaginal cavity, and is preferably non-wettable. The removal member 160 can be a piece separate from the vaginal insert device 100 or can be integrally formed with the vaginal insert device 100. When the removal member 160 is attached and/or formed with the vaginal insert device 100, pulling on the removal member 160 can cause the vaginal insert device 100 to inwardly collapse upon itself to reduce the largest lateral dimension or outer diameter of the vaginal insert device 100 to a removal diameter to provide an exemplary removal configuration. Preferably, the removal member 160 is connected to a portion of the proximal end 112 of the support segment 102. The removal member 160 has a shape suitable to be grasped so that the vaginal insert device 100 can be removed. For example, FIG. 2 shows the removal member 160 as a string.

In other aspects, the removal member 160 simply acts as a way to remove the vaginal insert device 100 from the vagina. In this exemplary removal configuration, the vaginal insert device 100 maintains the same shape and the same cross-sectional area so that the removal diameter is the same as the in-use diameter, D2.

The vaginal insert device 100 as described herein can be disposed after a single use, can be worn more than once, or can be reusable for a period of time (e.g., one week) before being disposed.

A method of manufacturing the vaginal insert device 100 is also disclosed. The method involves providing a vaginal insert device 100 as described herein having a distal end 110 and a proximal end 112. The vaginal insert device 100 includes a stabilizing segment 104 attached to the distal end 110 of the vaginal insert device 100, at least one fluid passageway 140 extending generally from the distal end 110 to the proximal end 112, and a removal member 160 attached to or formed with the vaginal insert device 100.

The vaginal insert device 100 is manufactured with a compliable resilient material. As used herein the specification and the claims, the term "resilient material" and variants thereof relate to materials that can be shaped into an initial shape, and subsequently formed into a stable second shape by mechanical deformation such as bending, compressing, or twisting the material. The resilient material then substantially reverts (or attempts to revert if constrained) to its initial shape when the mechanical deformation ends. The vaginal insert device 100 described herein is formed into the as-manufactured or relaxed configuration as described above. The vaginal insert device 100 can then be mechanically deformed for insertion or storage within an applicator 150. After the vaginal insert device 100 is inserted, the vaginal insert device 100 is restored to the in-use configuration 204 (which is similar to or smaller than the as-manufactured or relaxed configuration) due to the ability of the resilient material to relax or spring back to its original shape. Shape memory polymers can also be used.

Advantageously, the vaginal insert device 100 can be of a unitary construction and can be formed by molding an inert, biocompatible resilient polymer. In any event, the vaginal insert device 100, whether made of unitary construction or otherwise, is made of a suitable biocompatible material known to those of skill in the art. The vaginal insert device 100 can also be covered with a suitable biocompatible outer cover material. Desirably, the compliable resilient material can be formed from a closed-cell polyurethane foam.

After construction from the compliable resilient material, the vaginal insert device 100 can then be configured so that the support and stabilizing segments 102, 104 are compressed or folded inwardly such that the vaginal insert device 100 has an insertion diameter, D1. The vaginal insert device 100 can then be stored within an applicator 150.

In use, the vaginal insert device 100 begins in the insertion configuration 202. Desirably, the vaginal insert device 100 can be stored in the insertion configuration 202 within an applicator 150. The applicator 150 maintains the vaginal insert device 100 in the insertion configuration 202, and removal of the vaginal insert device 100 from the applicator 150 transitions the vaginal insert device 100 from the insertion configuration 202 to the in-use configuration 204 after insertion into the vaginal canal 26. The insertion configuration 202 includes the vaginal insert device 100 being compressed or folded inwardly so that the largest lateral dimension or outside diameter of the vaginal insert device 100 has an insertion diameter, D1. Alternatively, a user of the vaginal insert device 100 can configure the vaginal insert device 100 manually by compressing the vaginal insert device 100 inwardly prior to insertion with or without an applicator 150.

After insertion of the vaginal insert device 100 into the vaginal canal 26, the vaginal insert device 100 decompresses and expands to a maximum in-use diameter position in the transition between the insertion configuration 202 and the in-use configuration 204, wherein the largest lateral dimension or outside diameter of the vaginal insert device 100 has an in-use diameter, D2, larger than the insertion diameter, D1.

When ready for removal, the user will engage the removal member 160 on the vaginal insert device 100 and remove the device from the vaginal canal 26. When the vaginal insert device 100 is in the removal configuration, the largest lateral dimension or outside diameter of the vaginal insert device 100 can have a removal diameter that is the same size as the in-use diameter, D2. In other aspects, the vaginal insert device 100 can become elongated when the removal member 160 is activated so that the largest lateral dimension or outside diameter of the vaginal insert device 100 has a removal diameter smaller than the in-use diameter, D2. Desirably, the removal member 160 comprises a string, and tension on the string compels the vaginal insert device 100 to an elongated position in transition between the in-use configuration 204 and the removal configuration to facilitate easier removal.

In one aspect of the present disclosure, the vaginal insert device 100 can be part of a system in that it can be inserted using an applicator 150 similar to those known in the tampon art. The applicator 150 can be a push-type applicator or a retractable applicator. A collar can be added to control the depth of insertion. The applicator 150 can be dipped in a lubricant and placed into the vagina 12 until the base of the applicator 150 is at the opening of the vagina. In other aspects of the present disclosure, the vaginal insert device 100 can be inserted digitally/manually, or can be inserted using any other suitable apparatus.

After the user orients the applicator 150, the plunger then is pushed to its maximum extent, or until the user feels comfortable. The plunger and barrel are then removed from the body.

The vaginal insert device 100 can be enclosed in a flexible bag or covered with a skin that can reduce friction during deployment, help control the device during insertion and removal, help the device to stay in place, and/or create more contact area for applying pressure to the vaginal walls. For example, the vaginal insert device 100 can be enclosed in a vacuum shrink wrap plastic bag for insertion. Any medically-appropriate materials can be used to form the bag, and, depending upon the desired end use, the bag can be opaque, transparent, translucent, and/or breathable. Useful bag materials include those used in the manufacture of tampons, such as nonwoven fabrics and plastic film, including apertured films. The bag itself can also be apertured.

In exemplary aspects, the stabilizing segment 104 can be formed integrally with the support segment 102. In other aspects, the stabilizing segment 104 can be formed separately from the support segment 102 and attached by an attachment means, such as an adhesive. Similarly, the removal member 160 can be formed integrally with the support segment 102. In other aspects, the removal member 160 can be formed separately from the support segment 102 and attached by an attachment means, such as an adhesive or by tying.

In another exemplary aspect, the vaginal insert device 100 can also include an absorbent material. The absorbent material can surround or be included on or within one or both of the support and stabilizing segments 102, 104. In this aspect, the vaginal insert device 100 can be used as both a urinary incontinence device and a tampon that can be useful for absorbing body fluid from a woman's vagina, especially during her menstrual cycle. The absorbent material is coupled to the vaginal insert device 100 and is designed to be inserted above the introital region of the vagina. The absorbent material is designed to function to intercept the fluid flow of menses, blood, and other body fluids, and to prevent the fluid from exiting the vagina 12. It should be noted that, while in use, the vaginal insert device 100, with the possible exception of some or all of the removal member 160, will be positioned entirely within the vagina 12.

The absorbent material can be formed from absorbent fibers that are assembled into an absorbent sheet or ribbon. One exemplary type of sheet is described in patent application PCT/EP2004/006441 titled: "Airlaid Process With Improved Throughput," filed Jun. 16, 2003, and published Dec. 29, 2004 as WO2004/113608. Alternatively, the absorbent material can be formed from a general mass of absorbent fibers. In either case, the fibers are then rolled or assembled and compressed into a generally cylindrical and elongated shape. Two processes for forming such an absorbent sheet are known as "carding" and "airlaying." Depending upon the desired absorbency one desires in the finished tampon, the basis weight of the absorbent sheet can vary. The U.S. Food and Drug Administration (FDA) has set absorbency standards for "junior," "regular," "super," "super-plus," and "super-plus-plus" tampons. To meet the certain standards for these sizes, the absorbent sheets are targeted to have basis weights of about 100 grams per square meter (gsm), 120-150 gsm, 170-180 gsm, 210-230 gsm, and 240-260 gsm, respectively, and as much as 270-290 gsm. Typically, the formation process is controlled to produce an absorbent sheet with a width of between about 40 to about 60 mm, preferably about 50 mm. The basis weight and/or the length of the absorbent materials can also be adjusted to form the different size inserts.

The absorbent material is a plurality of fibers that are capable of absorbing. The first type of fiber (also referred to generally herein as binder fiber) is bondable to fibers of the plurality of fibers. Additionally, the plurality of fibers can be a homogeneous mixture of the types of fibers and additionally, or alternatively, the second type of fiber can have a material composition different than the first type of fiber. For example, the bondable first type of fibers can be polymer fibers. The absorbent material includes a second type of fiber that can be cellulosic fibers such as wood pulp, cotton, rayon, viscose, LYOCELL fibers from Lenzing Company of Austria, or mixtures of these or other cellulosic fibers. The second type of fiber can be a natural type fiber that might or might not be autogenously bondable to other like type fibers. The absorbent material can be a blend of viscose and binder fibers. Some blends that are believed to work well include a blend of about 70% viscose to about 95% viscose with the remainder about 30% binder fiber to about 5% binder fiber; and more advantageously about 85-90% viscose and the remainder about 15-10% binder fiber. The particular blend of fibers can vary depending upon preference in combination with achieving the features of the product.

More specifically, for example, the plurality of fibers can be either synthetic fibers or natural fibers, as long as the fibers have the desired absorbent and/or bondable characteristics. Synthetic fibers include those made from polyolefins, polyamides, polyesters, rayon, acrylics, viscose, superabsorbents, LYOCELL regenerated cellulose, and any other suitable synthetic fibers known to those skilled in the art. Many polyolefins are available for fiber production, for example polyethylenes such as Dow Chemical's ASPUN 6811A linear low density polyethylene. 2553 LLDPE and 25355 and 12350 high density polyethylene are such suitable polymers. The polyethylenes have melt flow rates, respectively, of about 26, 40, 25, and 12. Fiber-forming polypropylenes include Exxon Chemical Company's ESCORENE PD 3445 polypropylene and Montell Chemical Co.'s PF304. Another fiber can be a bi-component polyester sheath and polyethylene core and known as T255 made by Trevira of Germany. Other polyolefins are also available. Suitable rayon fibers are 1.5 denier Merge 18453 fibers from Acordis Cellulose Fibers Incorporated of Axis, Ala. The fibers can be treated by conventional compositions and/or processes to enable or enhance wettability.

Natural fibers can include wool, cotton, flax, hemp, and wood pulp. Wood pulps include standard softwood fluffing grade such as CR-1654 (US Alliance Pulp Mills, Coosa, Ala.). Pulp can be modified to enhance the inherent characteristics of the fibers and their processability. Crimping can be imparted to the fibers, e.g., by conventional means. Curl can be imparted to the fibers, e.g., by methods including chemical treatment or mechanical twisting. Curl is typically imparted before crosslinking or stiffening. Pulps can be stiffened by the use of crosslinking agents such as formaldehyde or its derivatives, glutaraldehyde, epichlorohydrin, methylated compounds such as urea or urea derivatives, dialdehydes such as maleic anhydride, non-methylated urea derivatives, citric acid, or other polycarboxylic acids. Some of these agents are less preferable than others due to environmental and health concerns. Pulp can also be stiffened by the use of heat or caustic treatments such as mercerization. Examples of these types of fibers include NHB416, which is a chemically crosslinked southern softwood pulp fiber that enhances wet modulus, available from the Weyerhaeuser Corporation of Tacoma, Wash. Other useful pulps are debonded pulp (NF405) and non-debonded pulp (NB416) also from Weyerhaeuser. HPZ3 from Buckeye Technologies, Inc. of Memphis, Tenn., has a chemical treatment that sets in a curl and twist, in addition to imparting added dry and wet stiffness and resilience to the fiber. Other suitable pulps include Buckeye HP2 pulp and IP Supersoft from International Paper Corporation.

For the cellulosic fiber (e.g., viscose, rayon, etc.), the fibers should have a staple length of between about 5 to about 35 mm. The fibers should have a denier of between about 2 to about 6. Denier is a unit of fineness of yarn based on a standard of 50 milligrams (mg) for 450 meters of yarn. The fibers can have a circular, a bi-lobal, a tri-lobal cross-sectional configuration, or some other cross-sectional configuration known to those skilled in the art. The bi-lobal configuration has a cross-sectional profile that looks like a dog bone while the tri-lobal configuration has a cross-sectional profile that looks like a "Y." The fibers can also be bleached if desired.

When cotton fibers are used, the cotton fibers should have a staple length of between about 5 to about 20 mm. The cotton fibers should generally have a fiber size of between about 150 to about 280 microns. The cotton fibers can also be bleached if desired. Bleaching will make the cotton fibers whiter in appearance.

In another aspect, there is a kit containing at least two vaginal inserts devices as described herein. In this kit, the first vaginal insert device can have a first length and a first in-use diameter and the second vaginal insert device has a second length and a second in-use diameter. The second length is different from the first length, and the first in-use diameter is different from the second in-use diameter to allow a user to determine the size of vaginal insert device to be used.

Other modifications and variations to the appended claims can be practiced by those of ordinary skill in the art, without departing from the spirit and scope as set forth in the appended claims. It is understood that features of the various examples can be interchanged in whole or part. The preceding description, given by way of example in order to enable one of ordinary skill in the art to practice the claimed invention, is not to be construed as limiting the scope of the invention, which is defined by the claims and all equivalents thereto.

We claim:

1. A vaginal insert device comprising:

a support segment having a distal end and a proximal end, the support segment defining a support segment plane; and a stabilizing segment extending from the distal end of the support segment, the stabilizing segment defining a stabilizing segment plane, wherein the stabilizing segment plane is generally perpendicular to the support segment plane when the vaginal insert device is in an in-use configuration, wherein the support and stabilizing segments are portions of a single device torus, wherein one side of the device torus is attached to an opposite side of the device torus to form the support and stabilizing segments, and wherein the one side of the device torus is attached to the opposite side of the device torus by attaching a string around the device torus.

2. The vaginal insert device of claim 1, wherein a largest lateral dimension of the vaginal insert device has an insertion diameter when the vaginal insert device is in an insertion configuration, wherein the largest lateral dimension of the vaginal insert device has an in-use diameter when the vaginal insert device is in the in-use configuration, and wherein the in-use diameter is larger than the insertion diameter.

3. The vaginal insert device of claim 1, wherein the support segment and the stabilizing segment are each tori.

4. The vaginal insert device of claim 1, wherein a radial cross-section of the support segment has an insertion area when the vaginal insert device is in an insertion configuration, wherein the radial cross-section of the support segment has an in-use area when the vaginal insert device is in the in-use configuration, and wherein the in-use area is larger than the insertion area.

5. The vaginal insert device of claim 1, wherein the support segment has a support segment longitudinal length when the vaginal insert device is in the in-use configuration, wherein the stabilizing segment has a stabilizing segment longitudinal length when the vaginal insert device is in the in-use configuration, and wherein the support segment longitudinal length is larger than the stabilizing segment longitudinal length.

6. The vaginal insert device of claim 1, wherein the support segment has a support segment longitudinal length when the vaginal insert device is in the in-use configuration, wherein the stabilizing segment has a stabilizing segment longitudinal length when the vaginal insert device is in the in-use configuration, and wherein the support segment longitudinal length is generally equal to the stabilizing segment longitudinal length.

7. The vaginal insert device of claim 1, wherein the support segment has a support segment outside diameter when the vaginal insert device is in the in-use configuration, wherein the stabilizing segment has a stabilizing segment outside diameter when the vaginal insert device is in the in-use configuration, and wherein the support segment outside diameter is larger than the stabilizing segment outside diameter.

8. The vaginal insert device of claim 1, wherein the stabilizing segment plane is generally perpendicular to the support segment plane when the vaginal insert device is in an insertion configuration.

9. The vaginal insert device of claim 1, Wherein the stabilizing segment plane is generally parallel to or coplanar with the support segment plane when the vaginal insert device is in an insertion configuration.

10. The vaginal insert device of claim 1, further comprising a removal member attached to one or both of the support and stabilizing segments.

11. The vaginal insert device of claim 1, wherein a largest lateral dimension of the vaginal insert device has a removal diameter when the vaginal insert device is in a removal configuration, wherein the largest lateral dimension of the vaginal insert device has an in-use diameter when the vaginal insert device is in the in-use configuration, and wherein the in-use diameter is larger than the removal diameter.

12. The vaginal insert device of claim 11, farther comprising a removal member, wherein tension on the removal member compels the vaginal insert device to an elongated position in transition between the in-use configuration and the removal configuration.

13. The vaginal insert device of claim 1, comprising a compliable resilient material.

14. The vaginal insert device of claim 1, further comprising an absorbent material coupled to the vaginal insert device.

15. A vaginal insert device system comprising:

a vaginal insert device including a support segment having a distal end and a proximal end, the support segment defining a support segment plane, and a stabilizing segment extending from the distal end of the support segment, the stabilizing segment defining a stabilizing segment plane, wherein the stabilizing segment plane is generally perpendicular to the support segment plane when the vaginal insert device is in an in-use configuration, wherein the support and stabilizing segments are portions of a single device torus, wherein one side of the device torus is attached to an opposite side of the device torus to form the support and stabilizing segments, and wherein the one side of the device torus is attached to the opposite side of the device torus by attaching a string around the device torus; and an applicator coupled to the vaginal insert device when the vaginal insert device is in an insertion configuration.

16. The system of claim 15, wherein a largest lateral dimension of the vaginal insert device has an insertion diameter when the vaginal insert device is in the insertion configuration, wherein the largest lateral dimension of the vaginal insert device has an in-use diameter when the vaginal insert device is in the in-use configuration, and wherein the in-use diameter is larger than the insertion diameter.

* * * * *